(12) United States Patent
Ogino et al.

(10) Patent No.: US 7,788,110 B2
(45) Date of Patent: Aug. 31, 2010

(54) MEDICAL CARE SUPPORT SYSTEM

(75) Inventors: Hirokazu Ogino, Tokyo (JP); Atsushi Kotake, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 2665 days.

(21) Appl. No.: 10/123,515

(22) Filed: Apr. 17, 2002

(65) Prior Publication Data

US 2003/0200114 A1    Oct. 23, 2003

(51) Int. Cl.
*G06Q 50/00* (2006.01)
(52) U.S. Cl. .............................................. 705/2; 705/3
(58) Field of Classification Search .................. 705/2, 705/3
See application file for complete search history.

(56) References Cited

U.S. PATENT DOCUMENTS

| | | | | |
|---|---|---|---|---|
| 5,113,859 A | * | 5/1992 | Funke | 607/4 |
| 5,664,110 A | * | 9/1997 | Green et al. | 705/26 |
| 5,724,580 A | * | 3/1998 | Levin et al. | 707/104.1 |
| 5,752,976 A | * | 5/1998 | Duffin et al. | 607/32 |
| 5,944,659 A | * | 8/1999 | Flach et al. | 600/300 |
| 5,967,986 A | * | 10/1999 | Cimochowski et al. | 600/454 |
| 5,978,855 A | | 11/1999 | Metz et al. | |
| 6,168,563 B1 | * | 1/2001 | Brown | 600/301 |
| 6,221,009 B1 | | 4/2001 | Doi et al. | |
| 6,612,986 B2 | | 9/2003 | Doi et al. | |
| 2001/0042024 A1 | * | 11/2001 | Rogers | 705/26 |
| 2002/0082480 A1 | * | 6/2002 | Riff et al. | 600/300 |
| 2002/0103505 A1 | * | 8/2002 | Thompson | 607/1 |

FOREIGN PATENT DOCUMENTS

| | | |
|---|---|---|
| JP | 8-38435 | 2/1996 |
| JP | 10-124601 A | 5/1998 |
| JP | 2001-243323 | 9/2001 |

OTHER PUBLICATIONS

English translation of the cited portions (paragraphs 0049 and 0056-0058) of JP 10-124601.

* cited by examiner

*Primary Examiner*—Robert D Rines
*Assistant Examiner*—Joseph Thomas
(74) *Attorney, Agent, or Firm*—Sughrue Mion, PLLC

(57) ABSTRACT

The present invention intends to provide various medical-related service by connecting the Medical Application Service Provider (MASP), which is a new institution providing medical care support service, and multiple medical institutions through private lines or general communication network including Internet Connection. The present invention provides the system that receives and transmits medical information among the Medical Application Service Provider (MASP) 2 and online terminals 4-1 to 4-4 placed at the medical institution 4 through the communication line 3. The MASP carries out process of medical data, responding to orders from online terminals, and transmits results to the online terminals placed at the medical institution. Further, the order of medical supply can be transmitted from the online terminal of the medical institution to MASP 2 and processed to efficiently deliver the medical supply.

2 Claims, 2 Drawing Sheets

MEDICAL CARE SUPPORT SYSTEM

BACKGROUND OF THE INVENTION

1. Field of the Invention

The present invention relates to a medical care support system, which improves medical service.

2. Related Art

Recently, introduction of computer technology is increasing in health care fields. For example, medical examination equipment, such as medical electronic devices, has been added a new function by adopting computerized data processing technology. Also, medical institutions have implemented data processing computer systems, which process diverse patient information such as reception, consultation, record of medication, and remuneration for medical service.

These conventional applications of computer technology in health care fields have been limited to stand-alone type medical examination equipment and to process of medical data within a medical institution or institutions belonging to the same chain. Thus, data processing technology has not been applied to process of medical data between medical institutions and other organizations through network.

Namely, conventional applications of computer technology have been limited to stand-alone type medical examination equipment and to relatively small size networks, which are constructed within a medical institution or institutions belonging to the same chain.

SUMMARY OF INVENTION

Accordingly, an object of the present invention is to reduce medical managing cost for a medical institution by putting out the institution's medical information procession with Application Service Provider (ASP) via communication network.

To achieve the above object, there is provided medical-related service by connecting Medical Application Service Provider (MASP), which is a new institution for providing medical care support service, and multiple medical institutions through private network or general communication network including Internet Connection.

To be more precise, there is provided a medical support system for communication among a online terminal at a medical institution and the medical application service provider (MASP) via communication network, wherein the online terminal comprising: (a) sensor or probe for detecting biological signals; (b) A/D converter for converting the biological signals to digital data; (c) first transmitting means for transmitting the digitalized biological signals; (d) first processing means for receiving and processing the data received from the medical application service provider; (e) display for displaying data; and the medical application service provider comprising: (f) receiving means for receiving the digitalized biological signals from the first transmitting means of the online terminal; (g) second processing means for processing the received biological data in response to demand from the online terminal; (h) second transmitting means for transmitting result obtained by processing of the biological data by the second processing means to the first processing means of the online terminal and for transmitting a viewer application for processing the result to be viewed to the first processing means of the online terminal; wherein the first processing means downloads the viewer application, receives the result and displays the result by executing the viewer application on the screen of the display of the online terminal.

Further, MASP having electronic medical chart application forms the results of procession of the biological signals transmitted from the online terminal in the medical chart manner, and provides electronic medical charts.

An object of the second aspect of the present invention is to reduce distribution costs for medical institutions and to make services more efficient by ordering system for ordering medical supply to MASP server via communication network.

To achieve the above object, there is provided a medical support system for communication among an online terminal at a medical institution, a medical application service provider and an online terminal of sales office via communication network, wherein the online terminal of the medical institution comprising: (a) means for input medical supply information for order; (b) first transmitting means for transmitting the medical supply; the medical application service provider comprising: (c) receiving means for receiving the order of the medical supply from the first transmitting means of the online terminal; (d) inventory affirmation means for affirming inventory information of the medical supply to data server in which inventory information is administrated; (e) notifying means for transmitting a notice to deliver the ordered medical supply to an online terminal of a sales office in charge of the medical institution.

Additionally, MASP has request means for transmitting a request to manufacturing the medical supply to a system of producing department when affirming that the medical supply is out of stock.

Further, MASP has selection means for selecting a sales office to deliver the ordered medical supply to the medical institution from one of sales offices which stand within the area where supplier at the sales office is able to deliver to the medical institution, on the basis of the inventory information of each sales office within the area; and transmitting means for transmitting notice to deliver the ordered medical supply to the online terminal of the sales office selected by the selection means.

Furthermore, MASP has price determination means for determining price of ordered medical supply in response to required delivering due period or numerical quantity.

Also, MASP has delivering administration means for administrating delivered medical supply with lot number or production serial number; and information transmitting means for transmitting information regarding to the delivered medical supply specified by the lot number or the production serial number to the online terminal of medical institution to which the ordered medical supply is delivered.

An object of the third aspect of the present invention is to support hospital managing by providing the hospital managing information from processed information at MASP via communication network.

To achieve the above object, for example, MASP has statistical processing means for processing statistical procession of at least one of number of admission patient, number of ambulant patient, utilization ratio of beds, and average length of stay at hospital for supporting hospital management.

DETAILED DESCRIPTION OF THE PREFERRED EMBODIMENTS

Hereinafter, preferred embodiments of the present invention will be concretely described with reference to the drawings.

Figure 1:
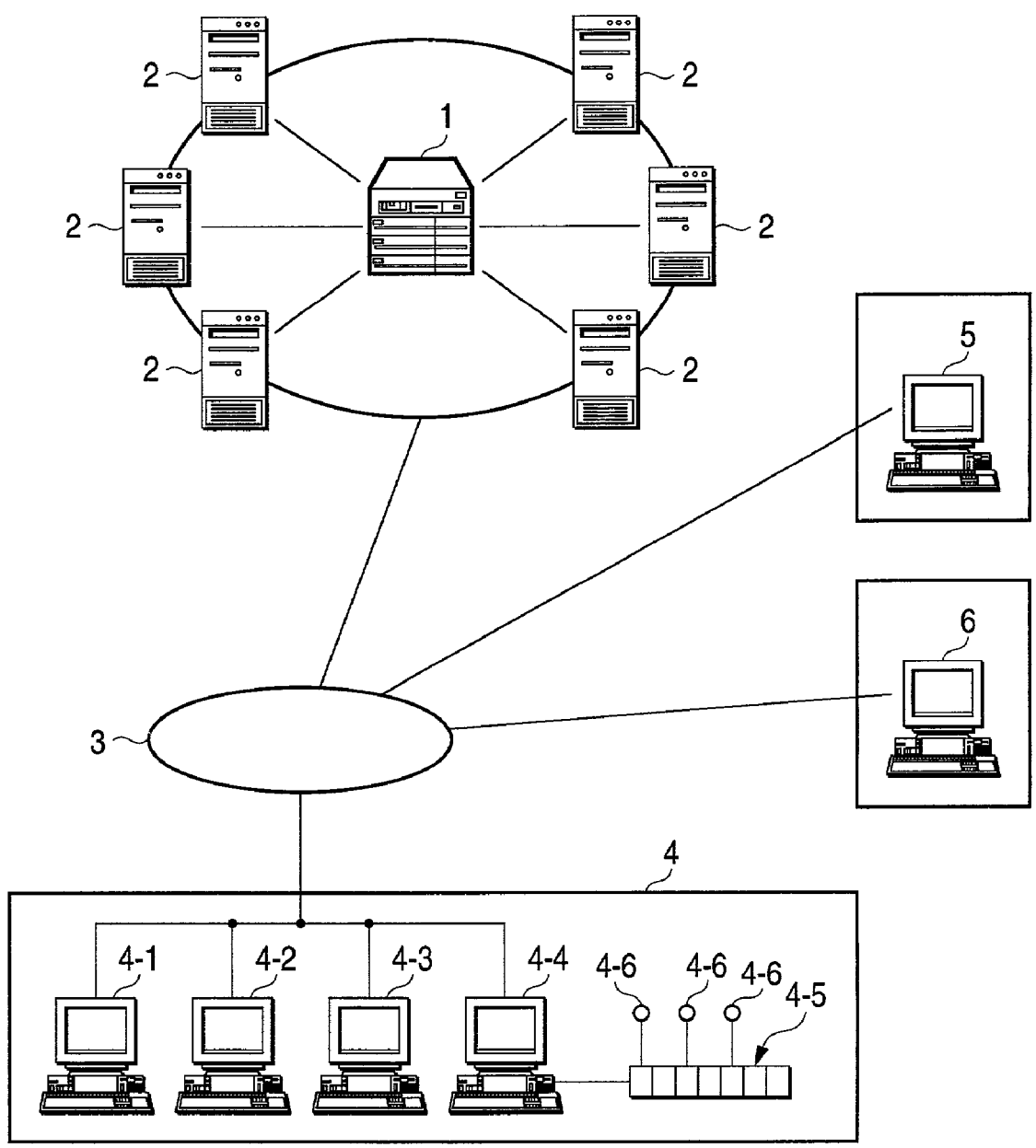
FIG. 1 shows the system configuration of the present invention.

In FIG. 1, 1 denotes a data server, and 2 denotes the MASP servers, which provide various medical services to customers by collaborating with the data server. Although FIG. 1 shows multiple MASP servers (six), it is possible to set up with a single MASP server depending on the size of the system, alternatively. Also, in case when there are multiple MASP servers in the system, it is possible to distribute these MASP servers to respective regions for providing service, or to separate MASP servers with respect to content of services.

The MASP mentioned above have following services on board.

Physiological Examination Support System
Medical Practice Support System
Medical Supplies Ordering System
Management Support System
Statistical Work System
Etc.

Figure 2:
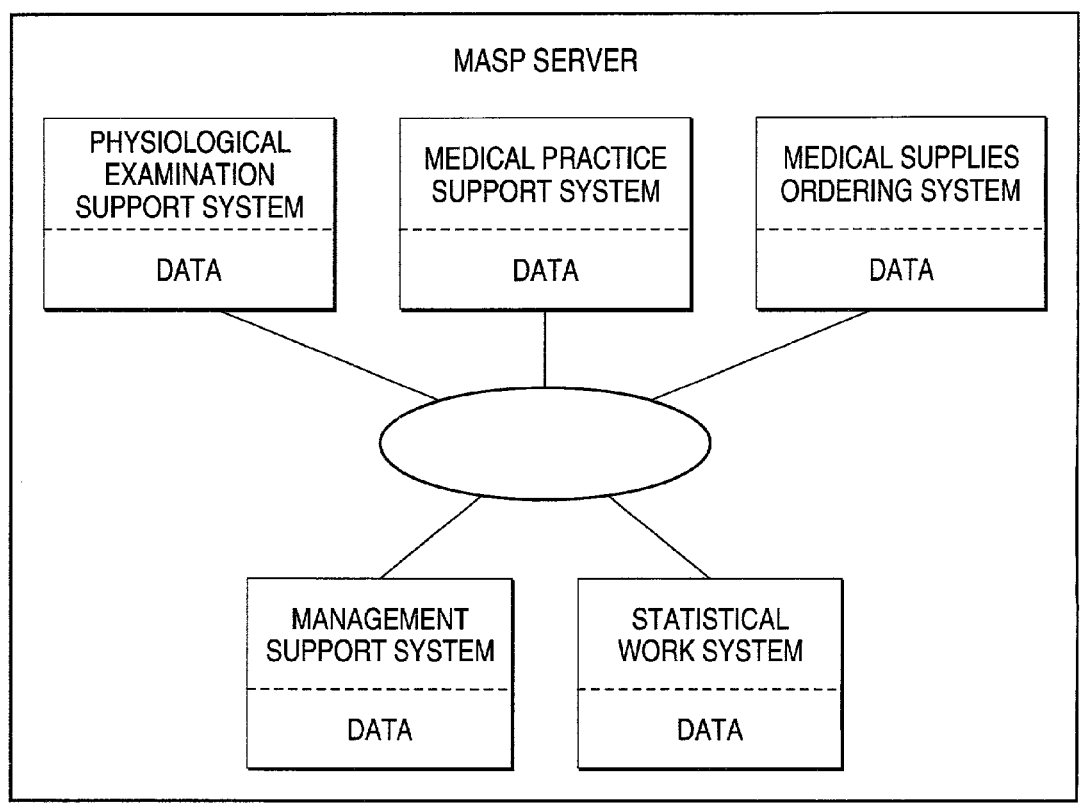
FIG. 2 illustrates the schematic of system structure of the MASP server 2.

FIG. 2 shows a schematic of the system configuration of the MASP server. It is possible to input and to output data of each system mutually, and also it is possible to share the data within the data server 1.

In FIG. 1, 3 denotes a communication network, which connects the MASP server mentioned above and customers' terminals placed at multiple medical institutions 4, sales offices 5, and distributors 6. Public telecommunication lines, wired or wireless private lines, or Internet network can be adopted as the communication network.

4 denotes a medical institution system of a customer, and the institution has an online terminal for the physiological examination support system 4-4, an online terminal for the medical supplies ordering system 4-2, an online terminal for the medical practice support system 4-3, an online terminal for the management support system 4-1, etc., which are corresponding to service content of the MASP server.

The online terminal for the physiological examination support system 4-4 mentioned above is connected with a measuring module 4-5 for connecting with multiple sensors. The measuring module 4-5 is connected with sensors or probes 4-6 attached to each patient.

The measuring module 4-5 mentioned above has various types such as a real-time ECG measuring module, a reading module for Holter ECG data, a real-time sonography module, temperature measuring module, blood pressure measuring module or blood test module, etc. It is also possible to substitute a measuring unit for a measuring module. Such biological signals are converted to digital signals and transmitted to MASP server for procession. The online terminal 4-4 has function of downloading viewer application, such as Java etc, for displaying the result of procession of the biological data processed by MASP server from MASP server, and executing the view application for displaying the result on the screen of the display of the online terminal 4-4. The viewer application may be installed to online terminal 4-4 previously, alternatively.

Furthermore, by transmitting medical image processing data, which is detected by examination equipment such as an endoscope, a CT, and a MRI, to an online terminal for the physiological examination support system 4-4 mentioned above, it is possible to process the data by the MASP server.

By employing such a physiological examination system, it is possible to automatically accumulate amount of analyzed data and interpretation data interpreted by medical doctor, which are measured by not only one but also many medical institutions, on the data server 1, it comes to be also possible to develop a new analysis method related to a new effective diagnose by processing the accumulated data by using various data processing methods.

In this case, each patient's data such as detected data and analyzed data should be treated carefully enough to satisfy the requests of a medical institution and patients, since it is sure that protection of individual privacy is critical and that deliberate treatment is indispensable to process the data. For example, it is necessary to separate individual information such as name, for processing the data.

5 denotes an online terminal placed at a sales office of a medical equipment sales company, which manages the MASP server 2. The online terminal 5 processes ordering of medical supplies, after a sales person receives an order from a medical institution, which is not connected with the communication network.

6 denotes an online terminal placed at a distributor, which is not affiliated to the company managing the MASP server 2. The online terminal 6 processes ordering and other requests to the MASP, after the distributor receives an order of medical supplies from a medical institution, which is not connected with the communication network.

All of the data server 1, the MASP server 2, online terminals placed at a medical institution 4-1 to 4-4, an online terminal placed at a sales office 5, and an online terminal placed at a distributor 6 connected through the communication network 3 have private addresses and centrally managed by the MASP server.

Also, patients who are caring by a medical institution 4 or home caring patients have private passwords, and the MASP server 2 recognizes individuals by using IC or magnetic cards, which are allocated to each patient.

Especially, in this kind of medical systems, it is indispensable to paying enough caution to manage a system at the same time to prevent individual privacy, because troubles such as distortion of patients cause critical medical accidents.

Therefore, medical information transmitted and received through a communication network is highly encrypted, and its content does not leak out to people outside. To protect individual privacy, the MASP server 2 takes all possible measures.

In FIG. 1, although there are six MASP servers 2 and the data server 1, it is possible to change the number of MASP servers and data servers based on size of the system. In other case, a MASP server can include a data server function together.

Also, in a medical institution mentioned above, it is possible to decrease the system's workloads such as data transmission by providing application service through a dedicated server installed in the institution. In this case, at least one of the several medical support systems is supplied from the dedicated server to online terminals placed within the institution.

In FIG. 1, although the medical institution has separate online terminals corresponding to content of services, it is possible to process several services by a single online terminal.

Also, a medical institution does not need to receive all services at once, and it is possible to make an agreement by choosing services necessary for each medical institution.

By downloading applications from the MASP server 2 and executing the downloaded application by an online terminal placed at a medical institution, operator of the terminal can easily execute an application to be used very often.

Hereinafter, content of each service provided by the MASP server 2 will be concretely described.

Physiological Examination Support System

A measuring module 4-5 connected with an online terminal for the physiological examination support system 4-4 is placed at each medical institution. Various modules are prepared for each necessary examination.

The detected data read from the measuring module 4-5 mentioned above is transmitted from the online terminal for the physiological examination support system 4-4 to the MASP server 2 through the communication network 3.

The detected data received by the MASP server 2 is analyzed in real time by the physiological examination support system.

In the case that the detected data from sensors or probes 4-6 is ECG data, each patient's data is transmitted after digitalized by A/D converter to the physiological examination support system in the MASP server 2 respectively, and the data is analyzed by an ECG analysis software of the physiological examination support system. The result of analysis such as arrhythmia analysis or R-R trend graph is sent back to the terminal 4-4 of the medical institution 4. The patient's data for transmission to MASP server 2 is preferably digitalized.

In the case that the detected data from sensors or probes 4-6 is real-time echocardiograph data, the data is digitalized by A/D converter and transmitted to MASP server 2. Then, the data of each patient's data is analyzed in real time by an echography analysis software of the physiological examination support system within the MASP server 2. Also, it is possible to send back the result of analysis such as a real-time heart volume analysis or a cardiac output analysis for each patient to the terminal 4-4 of the medical institution 4 by executing a 3-dimensional image processing added to a conventional 2-dimensional image of heart.

In other cases, it is possible to measure real-time data related to following examinations; electroencephalography, electromyography, respiration, temperature, blood pressure, blood test, etc. They are digitalized when transmitted to the MASP server 2.

Also, it is possible to send the data measured from a patient from an online terminal for the physiological examination support system to the MASP server as batch data. The batch data is read out periodically from a recorder such as a Holter ECG monitor, which is always carried by a patient, by using a reader device.

In this embodiment, the online terminal 4-4 is placed at a medical institution 4. However, it is apparent that the terminal can also be placed at a location such as a patient's home other than medical institutions, and it is possible to execute realtime examinations on a patient at the patient's home.

The data, which is processes by the physiological examination support system, is stored in the data server 1, classified into specific categories such as patient-base, examination-base, division-base and institution-base and calculated daily, monthly, and yearly.

The data server 1 properly analyzes the cost data incurred in examinations, classifies the data into specific categories such as patient-base, examination-base, division-base and institution-base, and adds daily, monthly, and yearly-calculated data. Then, the data server 1 charges the medical institution 4 the cost through the communication network 3 to the terminal of the medical institution 4.

Also, the data processing fee, analysis fee, storage fee and management fee are set in detail based on types of vital information data, amounts of data processing and storage, operating time, items of analysis, amounts of analysis data, software version of analysis, etc.

The medical institution 4 received this charge information pays timely the cost of physiological examinations, and at the same time the institution can use this information for charging each patient the cost needed for each examination.

To utilize for management of each division of the medical institution or the entire institution, the data mentioned above, which is classified into specific categories such as patient-base, examination-base, division-base and institution-base and calculated daily, monthly, and yearly, is also saved and used on the online terminal for the management support system 4-1 placed at the medical institution 4.

As merits of using the physiological examination support system for the examinations, the medical institution 4 does not need to purchase expensive physiological examination equipment and to employ operators for maintenance and monitoring of the equipment, by installing only the measuring module for physiological examinations 4-5.

Therefore, the medical institution can be provided a service, which requires latest and expensive physiological examination equipment, by paying only utility rate of each examination and rental fee of online terminals if the medical institution rent online terminals.

Also, the MASP server 2 can improve utilization ratio of expensive physiological examinations by contracting with many medical institutions.

The MASP server 2 can provide not only an analysis service for ordinary examination data, but also a security service such as an alarm service that transmits a department such as nurse station messages of disconnection of sensors or probes 4-6 from a patient by analyzing conditions of received detection data.

The Medical Practice Support System

The medical practice support system is the service, which can be provided by connecting the online terminal for the medical practice support system 4-3 placed at the medical institution 4 with the medical practice support system within the MASP server through the communication network 3. The system provides following services.

- Electronic medical charts function, which is related to reception service
- Therapeutic exercise, diet therapy, and nutritional instruction support functions
- Regional medicine, telemedicine, and home medical care support functions
- Medical-care program support function, such as critical path.

Hereinafter, the medical practice support services mentioned above will be concretely described.

Electronic Medical Charts Function

A medical doctor creates and saves a document as a medical chart, when he or she consults and treats a patient.

Since it is necessary to write a patient's condition in the medical chart at each consultation, the number of charts becomes very large if the patient has visited the medical institution for a log time. Also, if a patient takes consultations at several divisions, it is difficult to manage the medical chart by a form of paper documents because the chart has to include information, such as restriction of medication, mutually related to each consultation. Therefore, recently, medical institutions have begun to digitize medical charts to decrease the number of documents, and to make it possible to easily treat a medical chart among several divisions.

To digitize medical charts in the medical practice support system of the present invention, a doctor enters each consultation or treatment to the online terminal for the medical practice support system 4-2 placed at the medical institution 4 by filling out electronic documents according to instructions, and the entered information are transmitted to the MASP server 2 through the communication network. The entered information is saved within the data server 1. By adopting such a methods, the medical institution 4 can eliminate costs, which are necessary for installation of huge information processing equipment, its maintenance, and employment of its operators.

As shown in FIG. 2, the MASP server can read out a patient's measured and analyzed data from the medical examination support system mentioned above, and can file the data into the patient's electronic medical chart. Although real-time measuring data and analysis results become huge volumes of data, it is possible to save the data easily in each patient's electronic file and to use the data readily, by applying data processing such as data-compression.

Also, it is possible to transmit content of medical charts through a communication network even if receiving requirements from doctors belonging to different divisions in a same medical institution or doctors belonging to other medical institutions.

Therapeutic Exercise, Diet Therapy, and Nutritional Instruction Support Functions Health care interventions provided for patients at medical institutions include not only operations and medication conducted by doctors, but also therapeutic exercise for rehabilitation, diet therapy and nutritional instruction for inpatients.

Although nurses or dietitians who deeply comprehend patients' conditions have provided these conventional services for patients each and everyday, their workload has been quite heavy.

In the therapeutic exercise, diet therapy, and nutritional instruction support functions provided by the medical practice support system of the present invention, it is possible to create and transmit menus of therapeutic exercise, diet therapy, and nutritional instruction appropriate for each patient to the online terminal for the medical practice support system 4-3 placed at the medical institution 4 by receiving simple advice from doctors, nurses and dietitians, since the electronic medical charts, which comprehend patients' daily conditions as mentioned above, have been saved in the data server.

The MASP server 2 transmits menus of therapeutic exercise, diet therapy, and nutritional instruction appropriate for daily conditions of each patient, and can utilize the patient's daily record and conditions for improving his or her future medical treatment.

Also, it is possible to set a guideline based on statistical analysis of effectiveness of medical treatment by working with the physiological examination support system.

The medical institution 4 pays the service cost calculated daily, monthly, and yearly per each patient, responding to charges from the MASP server 2. However, compared with a conventional case that each medical institution provides same kinds of services independently, the costs are significantly reduced. Also, it is possible to use the latest and high-level menus of therapeutic exercise, diet therapy, and nutritional instruction appropriate for daily conditions of each patient.

Moreover, by working with the physiological examination support system and the medical charts system, it is possible to add functions such as evaluation of effectiveness of therapeutic instruction and creation of guidelines for medical treatments.

Regional Medicine, Telemedicine, and Home Medical Care Support Functions

The Regional medicine, telemedicine, and home medical care support functions provided by the medical practice support system of the present invention, consists of the MASP server 2 connected with the medical institution 4 through the communication network 3 and the online terminals placed at distant medical institutions or patients' homes.

In this system, it is possible to treat patients, who stay in distant hospitals, which have not employed specialists for their diseases, or take home medical cares, based on instructions of specialists who belong to the medical institution 4, by using the MASP server 2 as an intermediary.

In this case, it is also possible to provide raw data or analyzed data of examinations of each patient who stay in distant hospitals or take home medical care to doctors who treat the patients.

As the regional medicine support function, it is possible to manage all affiliated medical institutions effectively by promoting coordination between relatively small size regional medical institutions and large size urban medical institutions through the MASP server as an intermediary.

Medical-care Program Support Function, Such as Critical Path

It is difficult to decide each patient's schedule such as hospital admission, various examinations, operation, and treatment, based on judgment of only a single doctor.

Especially in a large medical institution, it is necessary to manage appropriate schedule based on time factors of all possible components in the institution, because such a large institution has many patients and doctors, and also several divisions have to share the same examination system with each other.

In the medical-care program support system provided by the present invention, it is possible to create and provide medical treatment schedules appropriate to each patient's condition by collecting various data from each medical institution and applying sophisticated system-planning software such as liner programming in the MASP server. As a result, it is also possible to make the best use of limited resources such as examination equipment and operation rooms. Also, it is possible to evaluate a course of treatment or its effectiveness by working with the physiological examination support system.

Especially in this system, it is possible to make a plan to use resources such as operation facilities, and examination equipment mutually among doctors or other medical institutions, responding to requirements.

The medical practice support system also charges utility rate based on application types of support functions and these used hours.

The Medical Supplies Ordering System

The medical supplies ordering system of the present invention conducts electronically ordering of medical supplies needed by a medical institution 4 connected with the MASP server 2 through the communication network 3.

Conventionally, sales persons belonging to sales offices of a medical supplies production and distribution company receive orders of medical supplies from their assigned medical institutions, and send orders to a sales department of the company.

In the medical supplies ordering system of the present invention, each medical institution 4 has the online terminal for the medical supplies (commercial product) ordering system 4-2, which provides input device, such as scanning bar code device or keyboard, for inputting order information such as type of medical supply, desired delivery due date, and the required number of medical supplies for a person responsible for ordering in the institution. The data inputted by the online terminal is transmitted immediately to the medical supplies ordering system of the MASP server 2 placed at a medical supplies production and distribution company.

The data server 1 manages inventory information of medical supplies. After receiving an order, the medical supplies ordering system accesses to the data server 1 and searches stocks of medical supplies corresponding to the order. If the ordered medical supply is not out of stock at the sales office in charge of the medical institution which orders the medical supply, the medical supplies ordering system of MASP server 2 transmits the notice to deliver the ordered medical supply to the medical institution to the online terminal of the sales office. If the ordered medical supply is out of stock, the medical supplies ordering system transmits a request of manufacturing immediately to a system of producing departments.

Also, by delivering the supplies directly to the institutions, it is possible to reduce distribution costs by simplifying distribution routes.

If there are inventory spaces of medical supplies in multiple regions, the medical supplies ordering system chooses the best inventory space for delivery to the medical institution, considering the institution's address and inventory conditions of inventory spaces.

For example, if each sales office has a stock of a medical supply, the inventory data is inputted from an online terminal placed at a sales office, and is managed in the data server 1.

Then, if a medical institution orders the supply, the medical supplies ordering system chooses a sales office, which is geographically possible to deliver the supply to the institution and has stocks of the supply, and sends a delivery direction as the ordering information to the online terminal 5 placed at the sales office.

The medical supplies ordering system manages proper inventory level of all medical supplies of the company by working with producing departments, considering ordering information such as ordering frequency.

Also, the medical supplies ordering system has a price setting function, and can decide uniformly a price of each medical supply, responding to conditions of orders. For example, it is possible to decide ordinary and extra charges based on desired delivery date, and to decide discount charges based on order quantity from each medical institution. It is possible to provide a clear price setting by adopting this kind of system.

The medical supplies ordering system, which received orders from a medical institution, transmits information such as names of ordered supplies, quantity, delivery dates, and charges to the online terminal for the medical supplies ordering system 4-2 placed at the institution. The online terminal 4-2 displays such received information. To finish the ordering operation, the institution checks the information, and transmits a confirmation message from the online terminal 4-2 to the medical supplies ordering system. Then, the medical supplies ordering system begins a delivery process according to the ordering information.

In the example mentioned above, a person responsible for ordering in the medical institution conducts ordering operation of medical supplies by using the online terminal for the medical supplies ordering system. In other cases, the medical supplies ordering system of the MASP server 2 transmits stock shortage information of each medical supply at each medical institution to online terminals for the medical supplies ordering system 4-2, by managing inventory of each medical supply stocked at each medical institution. This inventory information is based on analysis of consumption information of each medical supply at each medical institution. The consumption information is transmitted from an online terminal placed at each medical institution to the medical supplies ordering system continuously or periodically. Thus, it is possible to prompt a medical institution to order medical supplies before their stock shortage will occur.

Furthermore, by working with the physiological examination system and the electronic medical charts system, it is possible to manage proper inventory level and to output additional stock order information based on prediction of future consumption of medical supplies. The prediction is based on correlation analysis between patient data such as the number of patients classified by diseases, scheduled number of days in a hospital, items and the number of examinations, and consumption data such as medical supplies and medication needed for treatment.

Therefore, by using such an ordering system for ordering of medical supplies, it is possible to reduce personnel engaged in ordering operation of medical supplies at the same time to prevent miss-order.

Also, it is possible to use data, which is transmitted and received by this system, for many purposes, since the all data is saved in the MASP server 2 or the data server 1.

Medical supplies treated by this system are managed by their individual data such as lot number of production and serial number, and the data server 1 saves records of delivery information such as delivered institutions and delivery date.

Therefore, if precautions or trouble information of medical supplies should come to be noticed after delivery, it is possible to transmit the information immediately to online terminals for the medical supplies ordering system 4-2 placed at all medical institutions corresponding to the delivery records through the communication network.

It is also possible to transmit precautions of drug prescriptions in a case that the medical supplies ordering system treats medicines, and it is more efficient to work with the electronic medical charts system.

Medical supplies, which would affect human lives by result of use, have to be managed individually and thoroughly based on delivery information. In this system, it is possible to manage medical supplies easily and precisely because all delivery information of each medical supply is saved in the data server 1.

By asking medical institutions to transmit information such as usability and claims about medical supplies used in the institutions to the MASP server 2 through the communication network, it is possible to correct the information based on users' comments about medical supplies and to contribute to improvement of those medical supplies.

Also, it is possible to transmit announcements of new products to several medical institutions through communication network, and to form a community forum using communication lines among a medical supplies production, distribution company, medical institutions, and users of the supplies.

Since this system includes online terminals 5 placed at a sales office of a medical supplies production and distribution company, it is possible for medical institutions, which do not join in the system, to use the system in the same way as entering order information into the online terminal for the medical supplies ordering system 4-2 placed at the medical institution 4, by entering order information of medical supplies received from those institutions by sales persons into the online terminal placed at the sale office. In this case, a price setting function can set a different price for each medical supply based on judgment of a sales office, because the purpose of access to the system is different.

Moreover, since this system includes the online terminal placed at the distributor's office 6, it is possible to use the system in the same way as entering order information into the online terminal for the medical supplies ordering system 4-2 placed at the medical institution 4, by entering order information of medical supplies received from medical institutions, which do not join in the system, by the distributor's sales persons into the online terminal placed at the distributor's office.

In this case, a price setting function can also set a different price for each medical supply based on a contract with each distributor, because the purpose of access to the system is different.

The Management Support System

The management support system of the present invention, which consists of the MASP server 2 connected with the medical institution 4 through the communication network 3, treats managerial information such as utility rate of the physiological examination support system, utility rate of the medical practice support system, and charges of medical supplies ordered from the institution.

In the management support system, the data of the physiological examination support system is classified into specific categories such as patient-base, examination-base, division-base and institution-base, and calculated daily, monthly, and yearly. Also, the data is converted into visible formats such as circle graphs, bar graphs, or radar charts, then transmitted to the online terminal for the management support system 4-1, and displayed.

In the medical practice support system, cost information of menu creations for therapeutic exercise, diet therapy, and nutritional instruction, which are appropriate for daily conditions of each patient, is transmitted to the management support system and processed. Then, the result is transmitted to the online terminal for the management support system 4-1.

Also, cost information of medical supplies are classified into division-base, calculated daily, monthly, and yearly, and transmitted to the online terminal for the management support system 4-1 placed at the medical institution 4, to support management of the institution. In other cases, if the management support system processes cost data of expensive supplies such as examination equipment, the system provides additional information such as depreciation of the supplies based on these economic lives and cost estimations of renewal.

By using the information of electronic medical charts of the medical practice support system, the management support system can calculate daily, weekly, monthly, and average data such as 1) the number of inpatient, 2) the number of ambulant patients, 3) utilization ratio of beds, and 4) average length of stay at hospital, transmitted the data to the online terminal for the management support system 4-1, and display the data.

Furthermore, by applying approximation processing such as linearization, it is possible to transmit correlation information between processed data provided by those support system and income summary of medical institutions to the online terminal for the management support system 4-1, and display the data.

The data mentioned above contributes to management of a medical institution, because the manager of the medical institution can timely comprehend an effect of each factor on the income summary. Improvement of utilization ratio of beds, reduction of average length of stay, and improvement of medical care functions are conducive to improvement of income summary and management conditions.

The Statistical Work System

The statistical work system of the present invention stores huge amount of data, which includes information of electronic medical charts transmitted from many medical institutions 4 connected with the MASP server 2 through the communication network 3, in the data server 1. Thus, the statistical work system can make statistical works such as a survey on distribution of a disease in a specific region and its time-series analysis, by classified a lot of information of electronic medical charts into various groups such as regional-base, period-base, and disease base, and analyzing the data. It is also possible to estimate how many and what types of medical doctors will be needed in a region, based on the data mentioned above.

Moreover, the data is very useful for medical equipment manufacturers to coordinate production schedules of medical supplies, because it is possible to estimate demands of medicines or medical equipment, which are necessary for treatment of certain diseases.

As described mentioned above, the present invention proposes the new medical support system by inventing the medical application service provider (MASP), and this invention makes it possible for a medical institution to put out its medical examination support system to the MASP. Also, the MASP charges only utilization fee of examination support system based on the number and types of examinations processed by the MASP and rental fee of online terminals if medical institution rents the online terminals. Thus, a medical institution can carry out the latest examinations without investing huge amount of money to examination equipment, and at the same time can make computerized database of medical examination.

Furthermore, since the MASP can manage cost data of each examination of each patient and save the data in the system, it is possible to use the data for other services such as management support system, medical supply ordering system, and medical practice support system, by collaborating with other functions provided by the MASP. Therefore, the system of the present invention can provide not only technological innovation to conventional medical equipment, but also managerial innovation to medical institutions.

What is claimed is:

1. A medical support system, comprising:
   an online terminal, disposed at a medical institution;
   a sensor or probe, connected to the online terminal and adapted to detect a biological signal of a living body; and
   a server, disposed at a medical application service provider, and communicatively connected to the online terminal via a wide-area communication network, wherein:
   the online terminal comprises a first transmitter, operable to transmit the biological signal to the server via the wide-area communication network; and
   the server comprises:
   a processor, operable to process the biological signal transmitted from the online terminal, thereby generating biological signal data; and
   a second transmitter, operable to transmit the biological signal data to the online terminal via the wide-area communication network.

2. The medical support system as set forth in claim 1, wherein:
   the server is adapted to be communicatively connected to, via the wide-area communication network, a plurality of online terminals which are respectively disposed at a plurality of medical institutions; and
   the processor is operable to process a biological signal transmitted from any one of the online terminals.

* * * * *